US010111418B2

(12) United States Patent
Woodard et al.

(10) Patent No.: US 10,111,418 B2
(45) Date of Patent: Oct. 30, 2018

(54) ORGAN PERFUSION SYSTEM AND DEVICE

(71) Applicant: Perfusion Solutions Pty Ltd, Melbourne (AU)

(72) Inventors: John Woodard, Turramurra (AU); Ruchong Ou, Melbourne (AU); Jonathan Cavendish Nevile, Melbourne (AU)

(73) Assignee: Perfusion Solutions Pty Ltd, Melbourne (AU)

(*) Notice: Subject to any disclaimer, the term of this patent is extended or adjusted under 35 U.S.C. 154(b) by 318 days.

(21) Appl. No.: 14/891,879

(22) PCT Filed: May 26, 2014

(86) PCT No.: PCT/AU2014/000549
§ 371 (c)(1),
(2) Date: Nov. 17, 2015

(87) PCT Pub. No.: WO2014/194349
PCT Pub. Date: Dec. 11, 2014

(65) Prior Publication Data
US 2016/0113269 A1    Apr. 28, 2016

(30) Foreign Application Priority Data

Jun. 7, 2013  (AU) ............................... 2013902065

(51) Int. Cl.
*A01N 1/02*    (2006.01)

(52) U.S. Cl.
CPC ......... *A01N 1/0247* (2013.01); *A01N 1/0263* (2013.01); *A01N 1/0273* (2013.01)

(58) Field of Classification Search
CPC ... A01N 1/0263; A01N 1/0247; A01N 1/0273
See application file for complete search history.

(56) References Cited

U.S. PATENT DOCUMENTS

| 6,100,082 | A  | 8/2000 | Hassanein |
| 7,572,622 | B2 | 8/2009 | Hassanein et al. |
| 2006/0148062 | A1 | 7/2006 | Hassanein et al. |
| 2009/0197240 | A1 | 8/2009 | Fishman et al. |
| 2011/0177487 | A1 | 7/2011 | Simsir et al. |

OTHER PUBLICATIONS

"International Search Report and Written Opinion of the International Searching Authority", issued in International Application No. PCT/AU2014/000549 dated Jul. 7, 2014, Published in: AU.

*Primary Examiner* — Gautam Prakash
(74) *Attorney, Agent, or Firm* — Kaplan Breyer Schwarz, LLP

(57) ABSTRACT

A device and/or system for use in evaluation, transportation or storage of a donor heart, wherein the device comprises: a number of flexible membranes forming a sterile field around the heart; a first connector adapted to be attached into the membranes and a second connector attached with the membranes; wherein the first connector is adapted to secure and engage the aorta of the heart; and wherein the heart is partially suspended by the first connector.

15 Claims, 13 Drawing Sheets

ORGAN PERFUSION SYSTEM AND DEVICE

TECHNICAL FIELD

The present invention relates to relates to a device and system adapted for perfusing a donor heart or other organ during transportation.

BACKGROUND

Previously, there have been several attempts at developing transporting devices for carrying a donor heart. However, these previous devices have several major disadvantages.

One of main disadvantages of the previous systems and devices has been cost and complexity. These previous devices were not disposable and cheap to manufacture. Often previous devices included complex housing components or difficult to manufacture shapes. The materials used were often rigid and not suitable for transportation of a donor heart.

Some devices often rest the donor heart on a flat or concave surface with no or little cushioning for the donor heart and this may lead to occlusion or partial occlusion of the coronary arteries or veins that were in contact with the surface. The weight of the heart compresses upon the relatively rigid mounting surface and may occlude the arteries surrounding the heart. In the event of the anterior coronary arteries or veins becoming occluded, the perfusion solution will be unable to access the dependent areas of these vessels and the heart will quickly lose viability in these areas and the success rate of transplantation may be lower.

A further disadvantage with previous devices and systems is that they often rely on the outer wall of the rigid housing to encapsulate the donor heart during transport. If the housing is damaged, the sterile field surrounding the donor heart may be destroyed.

Other previous devices were adapted to perfusion of the organ by warm blood at pressures comparable to those encountered in vivo. The present invention is suitable not only for blood at near-physiological pressures but also for low pressure, low viscosity acellular colloid or crystalloid perfusion.

U.S. Pat. No. 7,572,622 discloses a similar device wherein a donor heart is cradled on a concave mounting surface within a housing. If the housing cracks or is damaged, the sterile field within the device is destroyed. Additionally, the full weight of the heart is positioned on the cradle wherein the coronary arteries may be compressed or occluded.

Any discussion of the prior art throughout the specification should in no way be considered as an admission that such prior art is widely known or forms part of common general knowledge in the field.

SUMMARY

Problems to be Solved

There has been a long felt need for a perfusion system or perfusion system that is adapted to perfuse a human heart during transplantation and in particular preserving the physiological condition and function of the heart and thus obtaining the best clinical result following transplantation.

It is an object of the present invention to overcome or ameliorate at least one of the disadvantages of the prior art, or to provide a useful alternative.

Means for Solving the Problem

A first aspect of the present invention may relate to a device for use in transportation and storage of a donor heart, wherein the device comprises: a flexible membrane or membranes forming a sterile field around the heart; a first and second connector attached to the membrane; wherein the first connector is adapted to secure and engage the aorta of the heart; and wherein the heart is partially suspended by the first connector.

Preferably, the first connector is adapted to be anchored and secured to relatively rigid housing by a mounting bracket. The location of this bracket may be made of variable height so that the amount of weight carried by the aorta and first connector can be optimized for different sizes of heart. Preferably, the first connector is adapted to allow for the delivery of perfusion fluid to the coronary arteries of the heart via the aorta.

The preferred housing, when in use, is adapted to encapsulate the membrane, and preferably the membrane forms a bag adapted to seal around the heart, when in use.

The preferred bag includes a region that opens to receive the heart and is resealable.

The second connector may be positioned beneath the heart and can include a one-way fluid valve adapted to allow used perfusion fluid to exit the membrane. It is preferred for no other contaminants to re-enter the sterile membrane surrounding the heart.

The membrane may include at least two electrodes mounted on an interior wall of the membrane adapted to contact the heart, when in use. The first connector may be connected to a perfusion pump and perfusion fluid reservoir using tubing.

Preferably, at least two electrodes are attached to leads wherein the leads are secured to walls of bag and exit through the first connector. The preferred housing includes a controller that controls the pumping rate of a perfusion pump, perfusion reservoir, and power source.

The preferred controller may selectively apply a defibrillation charge to the heart through applying electrical current to the defibrillation pad. The preferred housing includes a cushioned body mounted between a lower interior surface of the housing and the heart, wherein the cushioned body is adapted to support the heart and not provide pressure to the heart sufficient to compress or occlude the coronary arteries or veins.

A second aspect of the present invention may relate to a system for use in transportation and storage of an donor heart, wherein the device comprises: a flexible membrane forming a sterile field around the heart; a first connector being able to be easily sealed to the membrane and the second connector integrally formed with the membrane; wherein the first connector is adapted to secure and engage the aorta of the heart; and wherein the heart is partially or wholly suspended by the first connector.

Preferably, the first connector is adapted to be anchored and secured to relatively rigid housing by a mounting bracket. Preferably, the first connector is adapted to allow for the delivery of perfusion fluid to the coronary arteries of the heart.

The preferred housing, when in use, is adapted to encapsulate the membrane, and preferably the membrane forms a bag adapted to seal around the heart, when in use.

The preferred bag includes a region that opens to receive the heart and is resealable.

The second connector may be positioned beneath the heart and may include a one way fluid valve adapted to allow used perfusion fluid to exit the membrane.

The membrane may include at least two electrodes mounted on an interior wall of the membrane adapted to contact the heart, when in use. The first connector may be connected to a perfusion pump and perfusion fluid reservoir using tubing.

Preferably, at least two electrodes are attached to leads wherein the leads are secured to walls of bag and exit through the first connector. The preferred housing includes a controller that controls the pumping rate of a perfusion pump, the perfusion pump, perfusion reservoir, and power source.

The preferred controller or another specialised control system may selectively apply a defibrillation charge to the heart through applying electrical current to the electrodes. The preferred controller may selectively apply pacing impulses to the heart through applying electrical current to the electrodes. The preferred housing includes a cushioned body mounted between a lower interior surface of the housing and the heart, wherein the cushioned body is adapted to support the heart and not provide pressure to the heart sufficient to compress or occlude the coronary arteries or veins.

A second aspect of the present invention may relate to a device for use in transportation and storage of a donor heart, wherein the device comprises: a bag sealing around the heart to form a sterile field; a first connector being able to be easily sealed to the membrane and the second connector integrally formed with the membrane; wherein the first connector is adapted to secure and engage the aorta of the heart; and wherein the heart is partially suspended by the first connector, and wherein the bag is encapsulated within a rigid housing.

In the context of the present invention, the words "comprise", "comprising" and the like are to be construed in their inclusive, as opposed to their exclusive, sense, that is in the sense of "including, but not limited to".

The invention is to be interpreted with reference to the at least one of the technical problems described or affiliated with the background art. The present aims to solve or ameliorate at least one of the technical problems and this may result in one or more advantageous effects as defined by this specification and described in detail with reference to the preferred embodiments of the present invention.

DESCRIPTION OF THE INVENTION

Preferred embodiments of the invention will now be described with reference to the accompanying drawings and non-limiting examples.

A first preferred embodiment of the present invention is depicted in FIGS. 1-5. The first preferred embodiment includes a system and device adapted for the transportation and storage of a donor heart outside of a patient's body. The first embodiment is adapted to maintain the donor heart in a viable status for transplantation and the system or device may also include perfusion mechanisms, pacing mechanisms and defibrillation mechanisms to maintain the healthy functioning of heart even post death of the donor patient. Please note that the donor heart in this specification may also be referred to as ex vivo heart when the heart it outside of a patient's body and mounted within the embodied device or system.

In this specification, the sterile field means a specified area that is considered free of micro-organisms.

Figure 1:
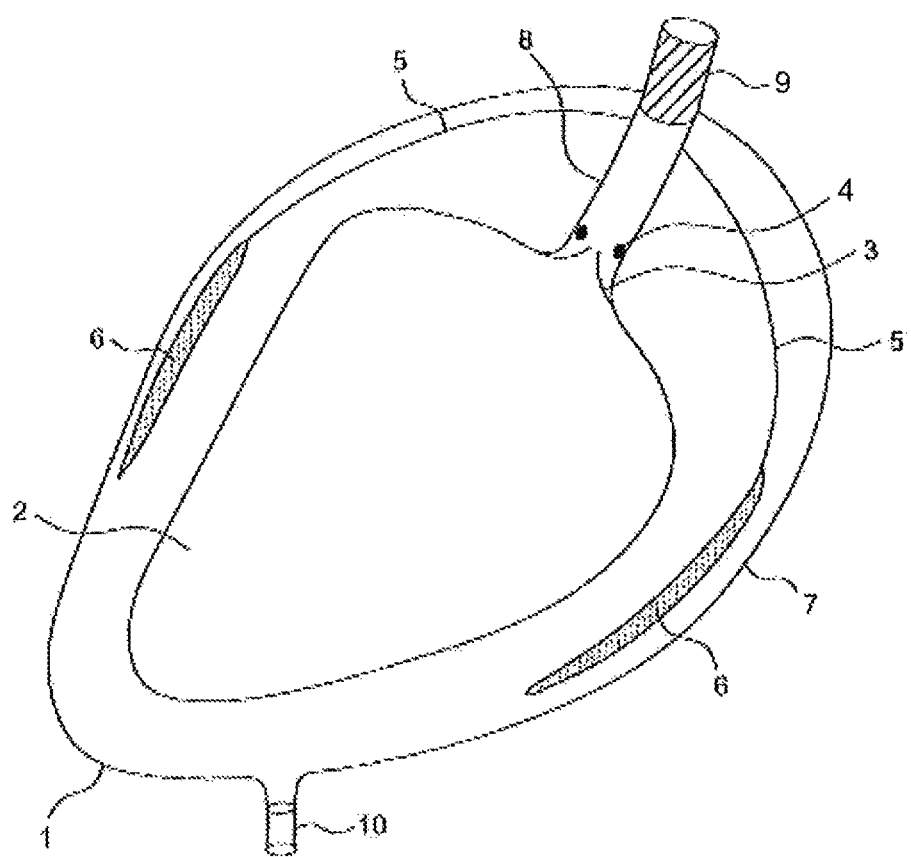
FIG. 1 depicts a cross sectional schematic view of a donor heart placing within a portion of the first embodiment of the present invention.

FIG. 1 shows a donor heart 2 mounted or positioned within a flexible sterile covering. In this embodiment, the flexible sterile covering or membrane or membranes are a specialised plastic bag (labelled 1 in FIGS. 1 & 2 and labelled 7 in FIGS. 3 & 6). The preferred characteristics of the bag 7 may include: flexibility, relatively water resistant to prevent fluid leakage, insulative properties in terms of electrical current, and provide a secure sterile environment for the heart. The bag 7 may opened at a selected region at the top of the bag 7 and sealed using a resealable lock or securing mechanism such as zip lock arrangement on the upper surface of the bag 7 (not shown). Preferably, bag 7 may also be able to be autoclaved without damaging the bag or otherwise sterilisable.

The bag 7 may provide a sterile field for storage and transportation of the donor heart between the time it has been explanted from the donor patient and being readied for implant into the recipient patient. Preferably, the bag 7 may also be transparent to allow for visual inspection of the heart 2 without breach the sterile field that occurs within the sealed interior of the bag, when in use.

The bag 7 of the first preferred embodiment is shown as including several preferred features: a first connector 9 adapted to secure and connect the heart 2 to the bag 7; a second connector 10 which may include function as a drain port and may include a one way fluid valve; electrodes 6 connected along wires or leads 5.

Figure 2:
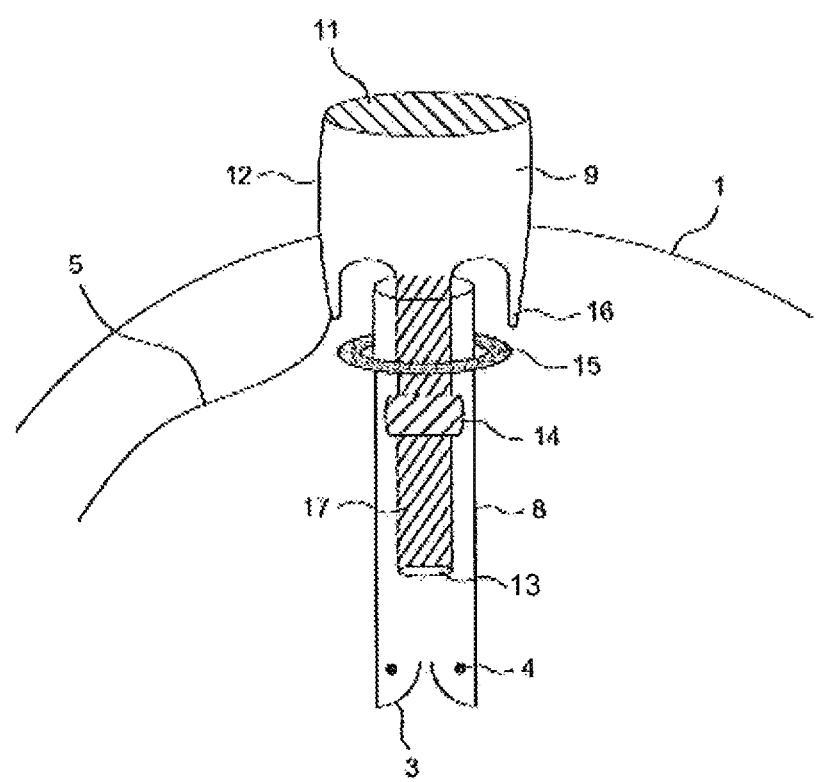
FIG. 2 depicts a cross sectional view of a further portion of the embodiment shown in FIG. 1.

The preferred first connector 9 is depicted in detail in FIG. 2. The primary function of the first connector 9 is to permit and enable fluid connection with the donor heart. The first connector 9 includes a main body 12 which is easily sealed to the bag 7. The first connector 9 includes a first end 11 and second end 13. The first end 11 is adapted to mate with a further connector (not shown) of a perfusion pump. The perfusion pump is adapted and modified to pump perfusion fluid into the donor heart to continuously perfuse the coronary arteries to maintain viability of the donor heart during transport.

The first connector 9 preferably includes a bore along the centre of the main body 12 connected the first 11 and second 13 ends. Preferably leads 5 are moulded into the first connector 9 to permit a feed through arrangement.

The first connector 9 may be constructed of a rigid and resilient material that is suitable for biocompatible purposes. Suitable materials for the first connector 9 may include PEEK, polyurethane, stainless steel, titanium or titanium alloys. The resilient nature of the first connector may allow for other connectors to interlock and also aid in the connection between the first connector 9 and the donor heart 2.

Preferably, the main body 12 is integrally joined a tube or spigot 17 which in turn leads to the second end 13. The second end 13 is adapted to be inserted within the aorta 8 of the donor heart 7. The spigot 17 preferably includes a securing means to secure and seal the aorta 8 around the outer surface of the spigot 17. At some location along the length of the spigot 17 is positioned an annular ring or protrusion 14 which is adapted to apply outward extending pressure to the inner wall of the aorta. Preferably, a tie mechanism 15 is secured in place along the outer wall of the aorta between the annular ring 14 and the main body 12.

Preferably, the bore of the spigot 17 is as large in diameter as possible given the diameter of aorta 8. This connector may be made in different sizes to suit different sized aortas. This feature may reduce leakage of perfusion fluid between aorta 8 and spigot 17. Further relatively large diameters of spigot 17 may enable increased relative flow rates (Q) and inversely reduced pressures (P).

Preferably, the first connector 9 may include a ridge or a collar or a protrusion 16 in a general annular shape extending from the lower surface of the first connector 9. This protrusion 16 may function to abut against the aorta 8, when in use. The protrusion 16 may also serve protect the connection between the first connector 9 and the aorta 8.

Preferably, the perfusion pump is adapted to pump perfusion fluid from a reservoir into the bore of the first connector 9, down through the middle of spigot 17 and then exit the perfusion fluid into the aorta 8. In this embodiment, the pressure of the perfusion fluid is enough to allow the leaflets of the aortic valve 3 to remain in a closed position. When the aortic valve 3 is in a closed position, the perfusion fluid is pushed into the coronary arteries 4 located proximal to the aortic valve 3 exit pathway. The perfusion fluid is then able to perfuse the heart 2 as the coronary arteries supply the perfusion fluid to the muscles of the heart. The used perfusion fluid exits the coronary arteries at the right side of the heart and is allowed to leak out and drain across the exterior surface of the heart 2.

The used perfusion fluid pools in the bottom of the bag 7 and preferably exits through the second connector 10, which is located on the lower surface of the bag 7.

Most perfusion fluids are suitable for use with this present embodiment, examples may include: oxygenated blood, Langendorff Preparation or other suitable commercial or experimental preparations.

In this embodiment, a second connector 10 is integrally joined and sealed to the approximate apex of the bottom of the bag 7. The second connector 10 is depicted in detail in FIG. 3. The second connector 10 includes a first 20 and second ends 21 joined by a main body with a bore running along the centre of the main body between the first and second ends.

In this embodiment, a one way valve 26 structure may be positioned in about the middle of the main body which enables pooled used perfusion fluid to exit the bag 7 but restricts its ability to re-enter the bag 7 after exiting the valve 26. The valve 26 comprises a relatively rigid leaflet support 24 in a Y shaped configuration with a small spigot 25 extending from the centre of the support 24. The spigot 25 is adapted to engage a flexible and resilient leaflet 23. The leaflet 23 preferably deflects to a raised position to allow the passage of used perfusion fluid out of the bag 7 via the valve 26. The leaflet may also deflect against the support 24 to seal the valve 26 in circumstances where the perfusion fluid builds up to a level outside the bag 7 to ordinary permit re-enter of used perfusion fluid, or to prevent gas entering the bag from this valve.

Figure 3:
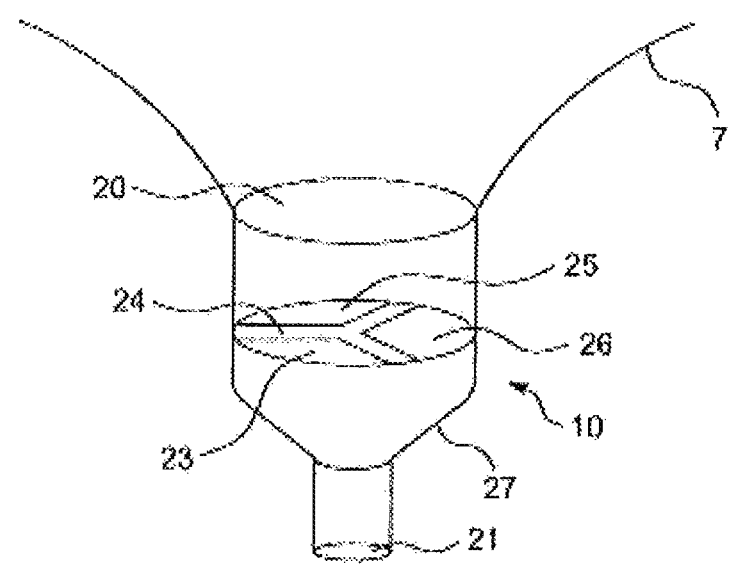
FIG. 3 depicts a cross sectional view of a further portion of the embodiment shown in FIG. 1.

Preferably, the second connector 10 may also include a flow adaptor 27. This flow adaptor 27 is shown in FIG. 3 as narrowed region between the first 20 and second 21 ends of the second connector 10 which may act to reduce or impede flow of the exiting perfusion fluid.

Preferably, the bag 7 may also include electrodes 6 mounted on the internal sides or walls of the bag 7. These pads 6 are positioned to contact the exterior sides or walls of the heart 2. In this embodiment, 2 pads are shown mounted adjacent or proximal to the positions of the right and left ventricles of the heart 2. Preferably, these pads 6 may be charged with electrical stimulation sufficient to initiate contraction of the appropriate side of the heart 2 or to selectively defibrillate the heart if and when a defibrillation event occurs during either transport or later evaluation of the heart 2 within this embodiment of the invention. Preferably, these pads 6 are large enough to encompass a large volume of the heart tissue.

Further, the heart may be quiescent during cold storage (e.g. not beating). This present device may be used for warm blood, in which case it could be either beating or fibrillating. When the heart is removed from the transport device, it may be then connected to a warm blood perfusion device.

Preferably, the bag 7 includes at least one pad 6 integrally attached to the inner wall of the bag 7. The pads 6 are electrically connected to wires or leads 5. These leads may be encapsulated within the walls of the bag 7 or may be attached by some other well-known means so long as the leads are electrically insulated so the electrical charge is not incorrectly applied to the wrong portion of the heart. Preferably, the leads 5 extend through the first connector 9 and are attached to a controller.

Figure 4:
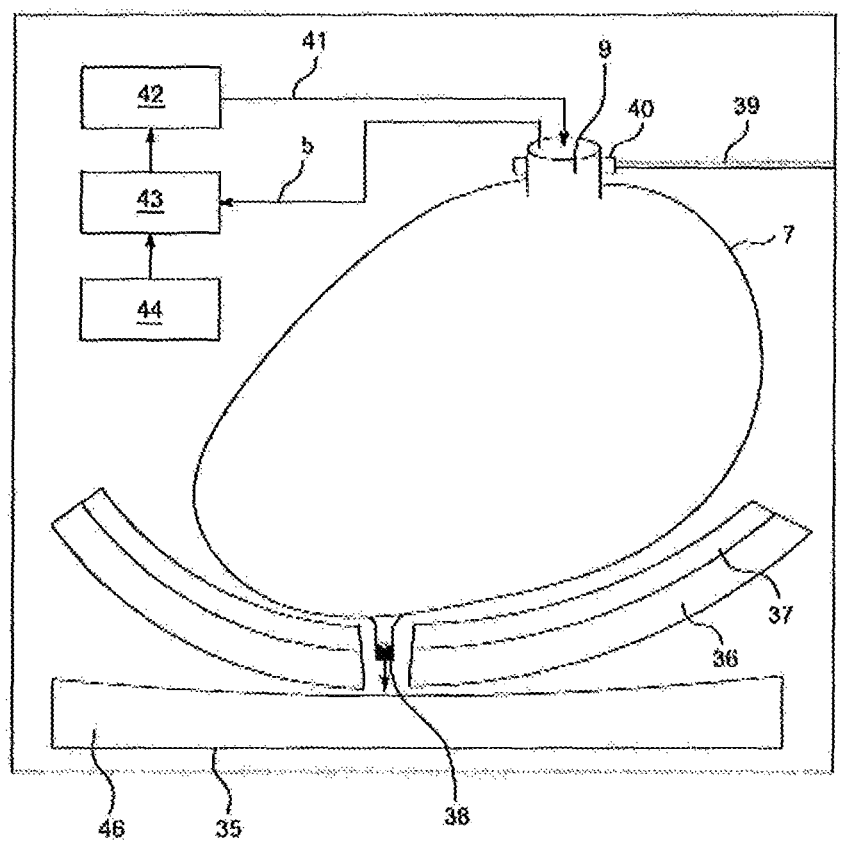
FIG. 4 depicts a cross sectional schematic view of the first embodiment showing additional housing features.
Figure 5:
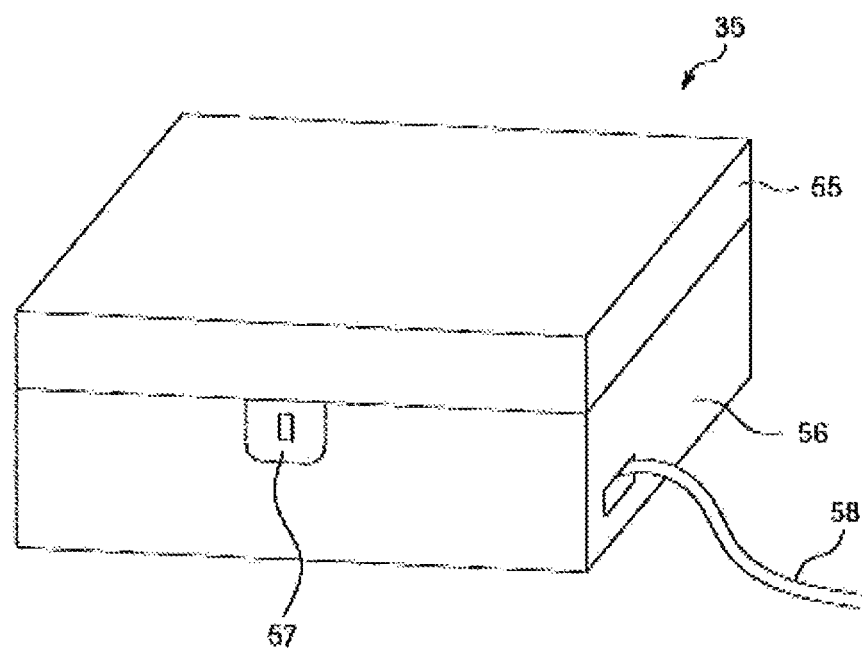
FIG. 5 depicts an exterior perspective view of the housing of the first embodiment as shown in FIG. 4.

FIGS. 4 & 5 depict the first preferred embodiment wherein a relatively rigid housing component 35. The housing 35 comprises an upper portion 55 and lower portion 56 joined by a hinge (not shown) positioned on the back of the housing 35. The front of housing may include a securing means or latch 57 which may be capable of securing the upper portion 55 in a closed position. The housing 35 may also include a sealing mechanism mounted between the facing surfaces of the upper 55 and lower portions 56. The seal is adapted to prevent contamination from entering the housing when the housing is sealed and secured in a closed position. The seal may also prevent accidental exiting of used perfusion fluid from the housing 35.

The housing 35 serves as a second layer of protection for the heart 2 when being transported. In previous transportation devices for transplanted organs, they typically only include a single layer of protection to protect the sterile field surrounding the heart. In this embodiment, there are two effective barriers protecting the sterile field or more if multiple bags are employed. The first barrier is the rigid housing 35 and the second barrier is the sealed bag 7. This configuration has the advantage of protecting the sterile field even if the housing seal is compromised by damage to it.

In this embodiment, the heart 2 is partially suspended within the housing 35. An arm or mounting bracket 39 extends from an interior wall of the housing 35 usually mounted on the lower portion 56. The mounting bracket 39 includes an engagement means 40 to lockably engage the first connector 9. The mounting bracket 39 is relatively rigid and may generally prevent or limit movement of the heart 2 when installed and in transport, but it may flex to allow some damping of potentially damaging shocks. In use, the mounting bracket 39 locks and secures the first connector 9 which is in turn secured to the Aorta 8 of the heart 2. In effect, the heart is being partially suspended by the mounting bracket 39. Aorta 8 is a relatively strong and resilient structure and is typically capable of carrying a large proportion of the weight of the heart. Further, the discussed suspension of the heart by the aorta allows for the aortic valve to be relaxed and uncompressed or restricted. This allows the aortic valve to form its natural relaxed shape so that the leaflets of the aortic valve form a seal to prevent fluid ingress into the left ventricle of the perfusion fluid.

Preferably, the suspension of the heart in the configuration shown in FIG. 4 may reduce the risk of the coronary arteries or veins from being occluded which may occur in previous devices which rely on cradles to support the heart.

In alternative embodiments, the mounting bracket 39 may include an adjustment means to allow the position of the heart 2 to be adjusted in the vertical axis when the heart is in the suspended configuration.

Preferably, the present embodiment may also include a relatively rigid support cradle 36 which may be flat or concave shaped. The lower surface of the heart 2 may lightly rest on the cradle and the cradle may give additional support to the suspended heart. Further the cradle 36 may include or compromise a cushion 37 which is mounted on surface of the cradle 36 between it and the lower surface of heart 2. The cushion 37 may be constructed of lightweight material that is compressible, flexible and resilient. In this embodiment, the cushion 37 is preferably constructed of foam or similar substance.

Positioned in the about the centre or middle of the cradle 36 is a relatively small gap 38 to allow for the protrusion of the second connector 10 of bag 7. The second connector 10 may extend through the gap 38 to prevent unnecessary pressure on the heart 2.

Preferably positioned below the cradle is a layer of absorbent material 46. This layer is adapted to absorb and soak up the extruded used perfusion fluid and to store it within the layer. Preferably, the layer may be constructed of absorbent sponge material.

The housing 35 may also include a perfusion fluid reservoir 42. The reservoir 42 is connected by tubing 41 to the first connector 9 of the bag 7. The reservoir 42 preferably holds and maintains a supply of fresh perfusion fluid suitable for perfusion to the heart. In this embodiment, the reservoir 42 also includes a small pump (not shown separately). The pump is preferably integrated within the reservoir 42 and the pump may be a small axial pump or centrifugal continuous flow pump.

The preferred housing may also be constructed of a transparent and relatively impact resistant material such as polyurethane or PEEK.

The pump is electrically connected to a controller 43 by wiring. The controller 43 is preferably configured to activate and control the pump. Preferably, the controller 43 may include various setting modes at which the pump may be instructed to run to provide perfusion support to heart.

Additionally, the controller 43 may be electrically connected to the defibrillation pads 6. If the controller detects the heart is experiencing a defibrillation event, the controller will automatically activate the pads 6. This feature will increase the viability of the heart whilst it is awaiting being implanted into the recipient patient. One additional advantage with the inclusion of defibrillation pads 6 within the interior of the bag 7, it that the heart 2 may be defibrillated without the surgeon or clinician broaching the sterile field conditions on the interior of the sealed bag 7.

Preferably, the controller 43 may be connected to a power supply or source 44. This power source 44 may be a battery or mains power. The power cord 58 for the mains power connection is shown in FIG. 5. Preferably, when mains power is in use this embodiment may use the mains power to charge the battery and run the controller. When the mains power is disconnected the system or device switches to using the battery only.

In alternative embodiments, a plug (not shown) may be constructed and shaped to allow placement and positioning within the first end 11 of the first connector 9. The plug may be selectively inserted to prevent contamination of the sterile field within bag 7.

The housing may also include a heater or cooler electrically connected to the controller 43 for heating the perfusion fluid in the reservoir 42. The heated perfusion fluid may be selectively used by to increase the temperature of the heart or to prevent damage of cold perfusion fluid. This heater may be integrated in the reservoir design.

Under certain circumstances, it may be preferred that the perfusion fluid be relatively cold to cool the heart 2 and preserve it from damage during transport. The housing 35 may also include a cooler which is connected to the controller 43 and the reservoir 42 and preferably cools the perfusion fluid prior to entry into the coronary arteries of the heart 2.

Preferably, in the above embodiments it is anticipated that the flow rates of the perfusion fluid may be less than 1 liter per hour during transport and storage. It may also be advantageous to increase the flow rates of perfusion fluid for evaluation purposes of heart to in the order 100-900 mLs per minute.

Prior to the introduction of the term "Brain death" into law in about the mid to late 1970s, all organ transplants from cadaveric donors came from non-heart beating donors (NHBDs). Donors after brain-dead (DBD), also known as beating heart cadavers, however, led to better results as the organs were perfused with oxygenated blood until the point of perfusion and cooling at organ retrieval, and so non-heart beating donors were generally no longer used except in Japan, where brain-death was not legally or potentially culturally recognized.

However, a growing discrepancy between demand for organs and their availability from DBDs has led to a re-examination of using non-heart beating donors, donors after circulatory death (DCDs), and many centers are now using such donors to expand their potential pool of organs.

Tissue donation (corneas, heart valves, skin, bone) has always been possible for non-heart beating donors. Many lessons have been learnt since the 1970s, and results from current DCDs transplants are comparable to transplants from DBDs.

NHBDs are grouped by the Maastricht classification:

| | | |
|---|---|---|
| I | Brought in dead | uncontrolled |
| II | Unsuccessful resuscitation | |
| III | Awaiting cardiac arrest | controlled |
| IV | Cardiac arrest after brain-stem death | |
| V | Cardiac arrest in a hospital inpatient | uncontrolled |

Categories I, II and V are termed uncontrolled and categories III and IV are controlled. Only tissues such as heart valves and corneas can be taken from category I donors. Category II donors are patients who have had a witnessed cardiac arrest outside hospital, have cardiopulmonary resuscitation by CPR-trained providers commenced within 10 minutes but who cannot be successfully resuscitated. Category III donors are patients on intensive care units with non-survivable injuries who have treatment withdrawn where such patients wished in life to be organ donors, the transplant team can attend at the time of treatment withdrawal and retrieve organs after cardiac arrest has occurred.

Prior to the present invention, all organs except the heart can potentially be used from category III, IV and V donors. The current device and system may be able to greatly increase the viability of donor hearts by better preservation of them during storage and transport. It may now be possible to extend the category of donors to category III, IV and V.

The present embodiments may be used to preserve donor hearts from patients who are already dead at the time of explantation.

Alternatively, it may also be preferred to include pressure and flow sensors within the reservoir or first connector and allow these sensors to feedback information regarding pressure and flow rates of perfusion fluid to the controller. The controller could activate an alarm, if the pressure rises indicating a blockage in coronary arteries of the heart or if the pressure falls indicating perfusion fluid leakage through the tubing or seals or through the aortic valve.

Additionally, the preferred embodiments may allow for inspection and evaluation of the viability of the heart 2 without needing to enter the sterile field. The inclusion of pressure or flow rate sensors also assists in this evaluation, and also the ability to inspect the preferred transparent bag 7.

Surgeons and clinicians can watch the donor heart through the transparent housing 35 and bag 7 and this reduces the need to remove the heart 2 from a sterile field until absolutely necessary.

The preferred embodiments also prevent recirculation of the used perfusion fluid which greatly reduces the risk of complications occurring during storage or transport.

Additionally, the bags 7 may be configured to be disposable and housing 35 could be reused with multiple donor hearts with no or little risk of cross contamination as the sterile field is primarily formed by the bag 7.

Additionally, bag 7 may marked to indicate the correct orientation of the heart when placed into the bag 7. This is to maximise the efficiency of the effect of the pads 6 when applying electrical current to the heart.

Preferably, when the heart is suspended within housing, the heart is positioned in almost a vertical orientation which follows the native orientation of the heart when in vivo.

Also, the one way valve 26 may be replaced with a labyrinth type seal to prevent regurgitive flow.

Figure 6:
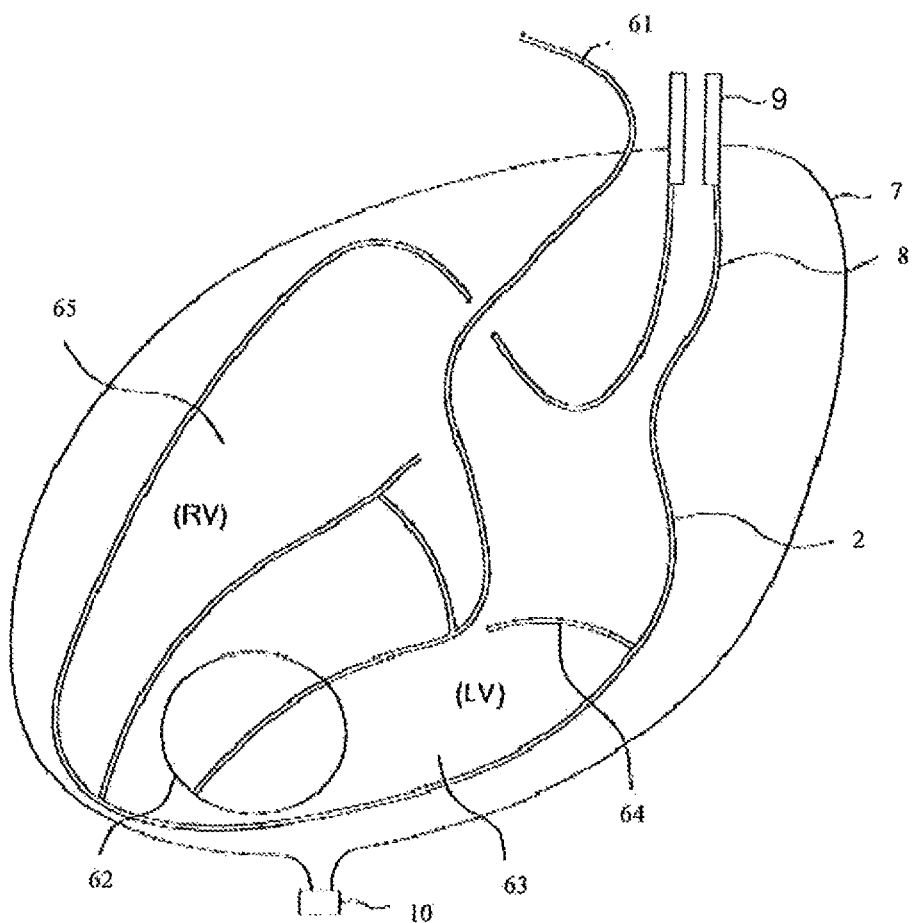
FIG. 6 depicts a cross sectional view of a further preferred embodiment, when in use with a heart.

A further preferred embodiment is shown or depicted in FIG. 6, wherein the interior of the heart 2 has been displayed. In this embodiment, the transport device includes the components and features of the earlier preferred embodiments, but additionally includes a cannula 61. Cannula 61 has been inserted into the heart 2 via the vena cava or similar available port open on the donor heart.

The cannula 61 includes a proximal end with a tip adapted for insertion within the left or right ventricle for transport of the heart. The FIG. 6 demonstrates the cannula 61 in the left ventricle 63 configuration. The cannula 61 is inserted into the left ventricle 63 and a balloon 62 is preferably inflated proximal to the proximal tip. Preferably, the balloon is adapted to fill the dead space of the left ventricle 63 and prevent the ingress of air but also may limit the dead space, which is occupied by non-circulating blood.

In this FIG. 6, the heart 2 is also shown to include: a right ventricle 65, and a mitral valve 64. Preferably, the cannula 61 enters through the mitral valve 64 and inhibits or limits the ejection of the left ventricle 63 through the aortic valve. Preferably, the cannula 61, when used in conjunction with the previous embodiments limits the opening of the aortic valve.

Preferably, the cannula 61 is flexible and hollow and allows for fluid or gas to pumped into the balloon for selective inflation or deflation. Preferably, the balloon is flexible and elastic and capable of inflating when fluid is applied to the interior of the balloon under pressure. The cannula may be connected to a pump for inflation.

Preferably, the balloon 62 may include an expansion limiter (for example an inelastic net or ribbing) to limit the expansion of the balloon so that it does not place undue stress on the interior walls of the heart which it may contact.

Alternate preferred embodiments of the present invention may also include a temperature probe mounted within the bag. Preferably, the temperature probe may be positioned, mounted, attached or integrated into the inner wall of the bag and be adapted to detect and monitor temperature within the bag and the space adjacent to the heart, when in use. Preferably, the temperature probe may be electrically connected to an external controller, as described with respect to the earlier described embodiments of the present invention.

Preferably, wires attaching the temperature probe or sensor may feedthrough the first connector in a similar fashion as the wires for the electrode pads.

In this embodiment, the temperature sensor or probe is adapted to feedback information to the controller where it may be logged or displayed. Generally, it is important that a donor heart is maintained at the correct conditions to improve viability of the heart during the transplant procedure. The controller may also alert users, if temperature falls or increases, beyond predetermined threshold values.

Figure 9:
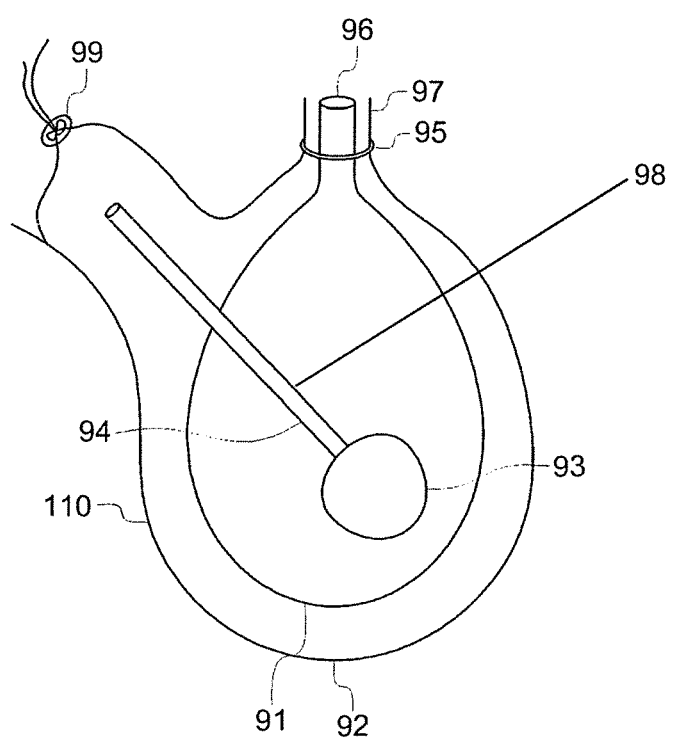
FIG. 9 depicts a cross sectional view of a preferred embodiment.

At least one further embodiment of the present invention is depicted within the FIGS. 7 to 10. In FIG. 9, a system or device 110 is shown wherein a heart 91 is encapsulated within a sealed a controlled environment such as sterile bag 92. An artery or vein 96 is positioned so as to pass through an aperture 97 in bag 92. The sides or walls of the aperture 97 may be selectively bound to the outer walls of the artery or vein 96 by the use of suture or flexible tie 95. This feature may seal the bag 92.

Preferably, the system or device 110 may be adapted or modified for use as either or both a transportation device or a cardiac evaluation device. The controller connected (not shown) may be adapted or modify to allow the system or device 110 to function in either mode.

The bag 92 may be replaced with further bags during either transportation stages or evaluation bags. Preferably, the bag is adapted to be a disposable or consumable item and not adapted to be reused.

A bottom valve (not shown in FIG. 9) may be connected to the bag 92. The bottom valve may incorporate a drainage valve (nearest apex of heart) which preferably is a one-way valve, and also a liquid out, no air back in valve—as the system has no air spaces or reservoirs in transport mode, except for the space where bubbles are initially caught, or caught in the system and released during transport (e.g. if a bubble happened to be trapped somewhere in the organ, or in the perfusion solution supply, proximal to the organ). The apex of the heart may be connected by cannulation.

An upper or top valve may be connected or integrated with the bag. Preferably, the upper or top valve may be adapted to be positioned or mounted on a connector joined to the aortic cannula or aorta. Preferably, this is a valved connector—i.e. there is a valve in the connector which allows outflow from perfusion solution reservoir 42 to heart bag in transport mode—this is to keep liquid from running out until the heart is connected, and to open immediately once the organ is connected, by simply connecting the aortic cannula to the other half of the connector, which is valved as described.

Figure 7:
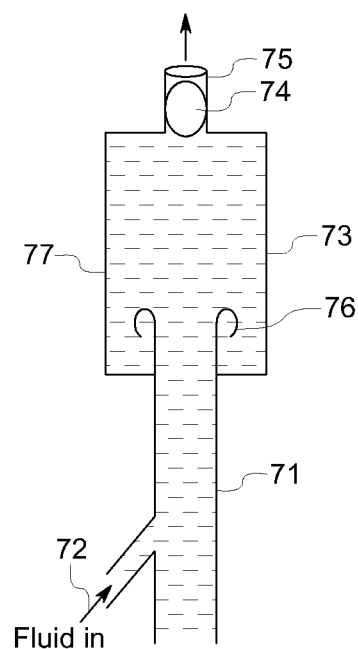
FIG. 7 depicts a side view of an embodied connector for use with the preferred embodiments.
Figure 8:
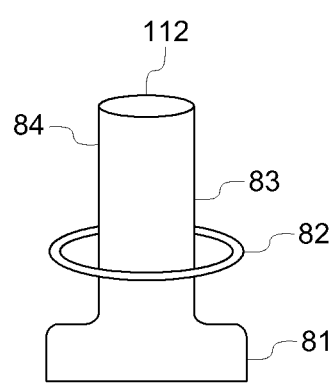
FIG. 8, depicts a side view of a further embodied connector for use with the preferred embodiments.

A preferred valve arrangement 77 is shown in FIG. 7. This valve may be used in place of any of the aforementioned valves. Cannulation 71 is adapted to be inserted into a main body 73, and further wherein the body is adapted to be wider or have a diameter greater than the cannulation 71. The cannulation 71 preferably includes a rounded lip 76 which is wider than the lower aperture of the main body 73 within which the cannulation 71 is inserted or positioned. The rounded lip 76 prevents the removal of the cannulation 71 without the disengagement of the main body 76. A person skilled in the art would appreciate that there are many methods that may be used to engage the cannulation 71 within the main body 73. At an opposed end of the main body 73 is an extension 75 adapted to capture air or gas bubbles 74 from the system. The extension 75 includes a one way valve to allow for the extrusion or removal of the bubbles 74 from the system without the ingress of fluids or gases from the outside environment.

Further the valve arrangement 77 may be adapted to incorporate a line in port 72 wherein perfusion fluid may be introduced into the system and pumped in. Preferably, the wider cross section area of the main body may allow for the gas to percolate from the perfusion fluid and to be trapped in the upper extension.

Preferably, the system has an additional liquid line provided by the aforementioned line in port (from its reservoirs or receptacles which collect the "used" perfusate) which is for re-circulation of the used solution back through the system and into the heart one or more times, to enable the system to be used in recirculation mode, if wished. This maybe the case if the device or system was being used on a very extended basis, and it was the fall-back option. This may also be the case if the perfusate was applicable for this kind of use.

Preferably, the ability of the system to add oxygenate the fluid if desired, and have this in situ so it can be used, or bypassed if not desired, via a small connected oxygenator from a portable oxygen supply (not shown)

Figure 10:
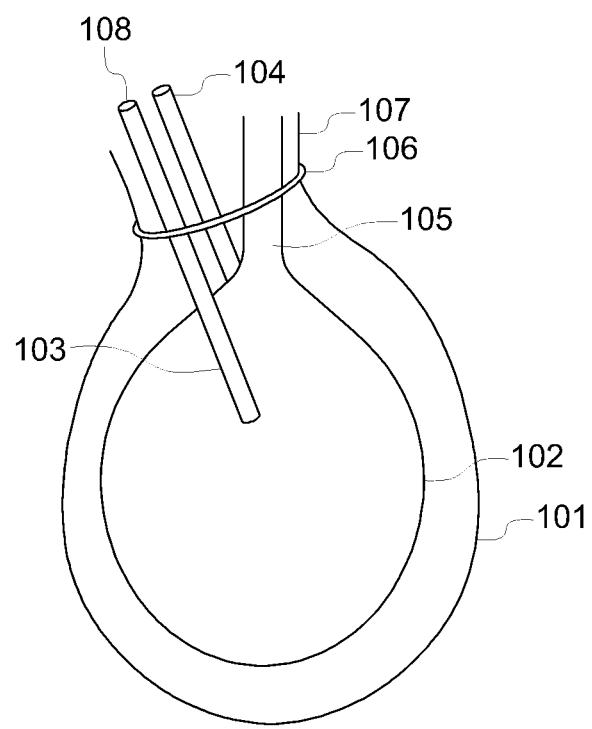
FIG. 10 depicts a cross sectional view of a further preferred embodiment.
Figure 11:
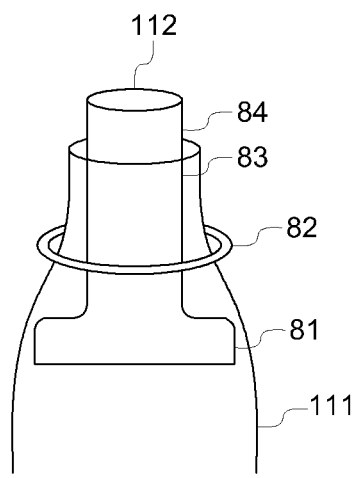
FIG. 11 depicts the connector of FIG. 8 in situ.

The present embodiment may also include a method to measure the cardiac efficiency and viability of the heart stored and transported within the preferred system. FIGS. 9 & 10, depicts two variations of achieving this feature. Preferably, one or more catheters may be inserted into the heart and a measurement balloon 93 inserted in through the sidewall of the bag 92 (as per FIG. 9), either via an unrolling/loose/flopping in piece of plastic, or via a sterile entry flap or entry system that wraps around the balloon catheter 98 in order to keep it sterile. Preferably, reaching into the bag, so the bag doesn't have to have it's sterility broken. Preferably, the cannula is sealed within the bag 92 by a tie 99. In FIG. 9, the balloon catheter is adapted to measure the efficiency or viability of the heart by the heart compressing the balloon tip 93 and changing the pressure within the balloon tip. The balloon catheter then is electrically connected to the controller and the controller may measure or report the pumping efficiency of the heart. In this embodiment, the balloon catheter 98 is inserted within a within an atrium, depending on placement.

The balloon catheter 98 includes an elongated body 94 and a balloon tip 93 which may be inflated or deflated by a surgeon or a machine. In this embodiment, the balloon tip 93 is preferably inserted into the interior space of a ventricle.

FIG. 10 depicts a similar configuration to FIG. 9, the bag 101 encapsulates the heart 102. However in this preferred embodiment as shown in FIG. 10, a first and second balloon cannula 104 and 108 have been inserted into the heart 102. The first balloon cannula 104 has been inserted into the right ventricle of the heart 102 and the second balloon cannula has been inserted into the left ventricle of the heart. Each insertion has achieved by extending into the heart by entering a respective access way in the heart. Preferably, the aorta is secured with an aortic adaptor 105, which is in turn adapted to be secured and engaged by the opening 107 of the bag 101. The opening 107 is scaled and tied by a flexible tic or suture 106. A balloon cannulas 104 and 108 may inserted within the heart wherein the respective balloon tip 103 is in a deflated position (please note that the balloon tip of the first cannula 104 is not visible from the visual angle of the FIG. 10). Preferably, a single tie 106 may be used to secure the first, second cannulas 104 and 108, and the aortic adaptor 105. In this manner, two balloon cannulas may inserted into the heart. Alternatively, the bag 101 may include a second opening separate from the first opening 107 within both cannulas could exit or enter the bag from in a similar manner to FIG. 9.

Preferably, two or more conductive pads, points or conductive mesh may be included or integrated with the bag and these may contact the heart on the inside of the bag—that measure ECG and allow for defibrillation, and that can determine (via the controller) which connections are best, and then preferentially use these for defibrillation, or instruct the operator which ones to use—by looking at the signal with the greatest amplitude if the heart forms a regular beating rhythm—this includes conductive points on the balloon catheter, which can be used to defibrillate sections of the heart between the catheter and the outer wall—so partial defibrillation of parts of the heart Preferably, the system or device of the preferred embodiment may include the ability to mount the bag (or the container which the bag is mounted in) on a one or more axis hinge (or gimbal-like system) for transport—to allow it to swing, for example during take-off and landing during a flight phase of transport, or during a sudden stop or small impact during road transit.

Preferably, the system or device may also include a integrated polymeric flexible mesh bag similar to "orange bag" style netting to support and to restrain the heart during transport.

Further, in these preferred embodiments, the system includes a preferred aortic cannula attachment management procedure or aortic connector 84 which herein described with reference to FIGS. 12, 8, 11, and 13:

a. via a clip to the top section of the aorta, or a clip, like a cir-clip arrangement or tie, that slides around the aorta, after it has been fit around the main body, and closes or is held closed by a latch or force around the aorta;

b. tied with tracheostomy tape to the top of the aorta—co-locating with one or more collars or rings on the aortic cannula which are designed to accommodate this, to hold the weight of the organ and fluids; or c. the aorta to be cable tied around the cannula
 1 with a stretchable cable tie, or
 2. a cable tie over flexible, soft rubber-like (such as silicone) tubing, or
 3. in a specially mounted piece of soft rubber-like (such as silicone) to provide even pressure between the aorta and the cannula beneath it, to hold it in place Preferably, aortic connector 84 may be inserted into the aorta 111 (also shown as 120). The connector 84 includes an elongated cylindrical body 83 having two ends. A first end is flanged outwardly and adapted to be inserted into the aorta 111. Preferably, the inner wall of aorta 111 engages the outer wall of the connector 84 and is secured or fastened in place by a tie 82. The tie 82 may be a cable tie, suture or some other flexible resilient biocompatible material.

Figure 13:
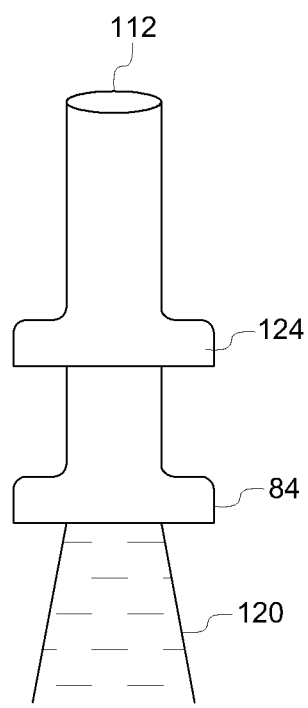
FIG. 13 depicts a side view of a preferred stack of connectors for use with the preferred embodiments.

The second end 112 of the aortic connector 84 is adapted to engage other cannulation as previously described within this specification. Additionally, the opposed second end 112 may be adapted to lockably engage a first end of a second connector 124. This allows multiple or a plurality of connectors to lockably connected to one another to form a stack as shown in FIG. 13.

Figure 12:
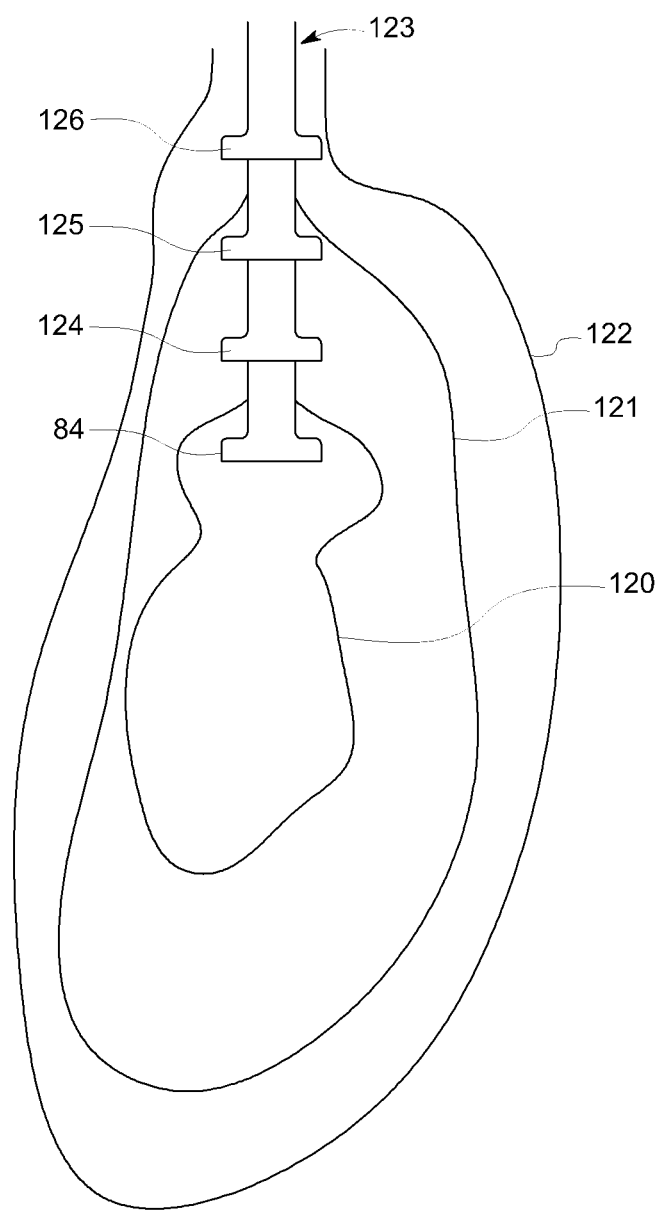
FIG. 12 depicts a cross sectional view of a further preferred embodiment.

The stack may be continued to include third and fourth connectors 125 and 126 as shown in FIG. 12. In FIG. 12, each respective connector engages either the aorta of heart 120 or a bag 121 or a second bag 122. This allows for the bag 121 to be restrained by a separate second connector 124 to the first connector 84 which is restraining the aorta and the heart 120.

Preferably, tie mechanisms mounted on the outside of the connectors may include cable ties. These cable ties may be tightened with a cable tie gun capable of being set to the correct pressure to hold the heart by prevent damage to the aorta—simple to use and repeatable, with averaged force and stretch across the whole clamping mechanism.

Preferably, the outwardly directed flanges 81 of the connector 84 may be replaced or include one or more collars (or soft rubber barbs) which are soft, rubbery, smooth and curved—like ribs—which some of the fixing mechanisms restrain the aorta to prevent unnecessary movement.

The device or system may include two different shaped tubes, where the first, thinner one is inserted into the aorta, and the second tube is slid down over the first, and the aorta, and squeezes on the aorta, locking it in place between the two, with either the inner tube expanding into a channel in the outer, pushing the aorta in between into this channel, and therefore holding it tight with known pressure, which may be adjusted via a locking (such as a screw) mechanism between the two cannulae.

Preferably, there are provided graduations along the cannula from the insertion tip, so the clinician can ensure that it's not inserted too far into the heart (e.g. about 2-3 cm from the heart valve, and about 1-2 cm from the cut (into the aorta)) in order to have enough room to hold the heart by the top 1-2 cm of the aorta, that will ultimately be cut off by the surgeon before it's attached to the recipient.

At the connector 77 as shown in FIG. 7, that the top of the cannula connects to, a "push/insert to open" valve in transport rig in order to allow the fluid to be filled, and engaged with minimum air entering the system, and preventing all of the perfusion solution from running out of the supply side, but allowing a large opening for de-airing when first connected, and when in use on the rig, say a bubble should be inadvertently get trapped somewhere in the heart.

Preferably, in the transport mode, a big and wide bubble trap above the heart—with a hydrophobic valve at the top of this reservoir of fluid, to allow any air out, and to keep the system free from air, and allow for bubbles of gas to escape, whilst not preventing the flow (or allowing fluid to flow out this valve), and to keep any air out of the heart, and away from the valve. This trap may include a wide bore bubble removing system with a hydrophobic filter/valve.

FIG. 12 depicts a preferred system or device wherein overlapping bags have been employed or utilised to improve sterility and resistance to breaking. Preferably, one or more inner bags—attaching to the aortic cannula to keep the heart sterile during the whole transportation or evaluation process.

Additionally, the usage of one or more outer consumable bags—mounted in an overlapping formation as shown in FIG. 12 may maintain or keep the inner bags and system sterile, and allow the organ and inner bags to be passed between a sterile and non-sterile area. For example, outer layer bags may be removed as the unit or device is transported between sterile zones to maintain the maximum level of sterility and avoid contamination by the outer surface of any one bags coming into direct contact with the heart upon removal from the device or system.

The above described stack 123 of one or more connectors (which may or may not be snap-on/quick connector) co-located with the bags mentioned above, so that a non-sterile nurse may pass the non-sterile bag across to the sterile line, where it can be disconnected simply using the connector, with the sterile theatre nurse only touching the inner connector, and this may then be passed to the surgeon ready for removal from the bag and implantation.

Preferably, the layers of bags may be cut off by the surgeon, to enable easy access to the organ, or the inner bags, or inner, bag mounted connectors.

It is preferred throughout these embodiments that the ties or fixing cable ties may be removable or cut off by a surgeon when the appropriate time arrives to remove the heart from the system.

Preferably, there may be more than one connector—like a T-piece or a Y-piece, with valves, to allow multi connections, or parts to stay within the sterile bag, so that if the non-sterile part is removed/cut off then the sterile connector remains for use, (e.g. on the evaluation rig).

Previous to the present invention, three layers of bags are often used for heart transplants procedure and transportation modes, with two inner, and one outer, removable bag—this invention uses a similar system, but adds the ability to use connectors to the aortic cannula to this system, and the ability to have through-bag ports, in the sides of the bag or bags, and connectors for measurement, and for electrical use for monitoring and defibrillation (not shown).

Preferably, the bag(s) are adapted to be constructed in such a manner as to enable pressure to be applied from the outside to defibrillation pads inside the bag, directly onto the organ for good electrical contact. The bags may also be partially constructed of electrically isolated sections of an electrically conductive polymer to allow for the conduct of electrical signals to the heart in the event of defibrillation.

Preferably, the bag of any of the preferred embodiments may be constructed so as to allow optical or ultrasound diagnostic measurements to be taken through the bag, sometimes with special glass or other material "windows" to facilitate this, and in other instances, straight through the plastic, e.g. SpO2, CO2, blood glucose, Doppler fluid flow and other optically or ultra-sonically useful measurements to be taken from the outside of the bag, without causing any harm to the organ or sterility of it. Preferably, construction materials of the sterile bag may include transparent or relatively transparent polymeric material, which is flexible, resilient and sterilisable.

Although the invention has been described with reference to specific examples, it will be appreciated by those skilled in the art that the invention may be embodied in many other forms, in keeping with the broad principles and the spirit of the invention described herein.

The present invention and the described preferred embodiments specifically include at least one feature that is industrially applicable.

The claims defining the invention are as follows:

1. A device for use in evaluation, transportation or storage of a donor heart, wherein the device comprises:
   a first membrane and at least one further membrane such that the first membrane is encapsulated by the at least one further membrane forming a sterile field around the heart;
   a plurality of connectors forming a stack, the stack comprising a first connector, a second connector and a third connector;
   wherein the first connector is adapted to secure and engage the aorta of the heart; and
   wherein the second connector and the third connector are engaged with the first membrane and the at least one further membrane, respectively, the first connector configured to partially suspend the heart and adapted to allow for delivery of perfusion fluid to the heart.

2. The device of claim 1, wherein the first connector is adapted to close an aortic valve of the aorta of the heart.

3. The device of claim 1, wherein the first connector is adapted to allow for the delivery of perfusion fluid to the coronary arteries of the heart.

4. The device of claim 1, further comprising a housing which encapsulates the membranes forming the sterile field.

5. The device of claim 4, further comprising a mounting bracket for securing the first connector to the housing, to limit the movement of the first connector.

6. The device of claim 4, wherein the housing comprises a cushioned body mounted between a lower interior surface of the housing and the heart, during the use of the device.

7. The device of claim 1, wherein each of the first membrane and the at least one further membrane form a respective first bag and at least one further bag adapted to seal around the heart, when in use.

8. The device of claim 7, wherein each of the bags comprise a region that opens to receive the heart and each said region is resealable.

9. The device of claim 7, wherein at least two electrodes are attached to leads and wherein the leads are secured to walls of at least one of the first bag and the at least one further bag and exit via a sealing mechanism of the first connector.

10. The device of claim 1, further comprising a valve in the first membrane adapted to allow used perfusion fluid to exit the first membrane forming the sterile field around the heart.

11. The device of claim 1, wherein the second connector comprises a one way fluid valve.

12. The device of claim 1, wherein the first membrane comprises at least two electrodes mounted on an interior wall of the first membrane adapted to contact the heart, when in use.

13. The device of claim 12, wherein the electrodes are adapted for at least one of pacing and defibrillation.

14. The device of claim 1, wherein the first connector is connected to at least one of a perfusion pump and a perfusion fluid reservoir using tubing.

15. The device of claim 1, wherein the device comprises a temperature probe mounted within the first membrane and wherein the temperature probe is adapted to detect the temperature of the heart, when in use.

* * * * *